(12) United States Patent
Okuda et al.

(10) Patent No.: US 10,137,250 B2
(45) Date of Patent: Nov. 27, 2018

(54) SYRINGE AND PREFILLED SYRINGE

(71) Applicant: Terumo Kabushiki Kaisha, Tokyo (JP)

(72) Inventors: Yuji Okuda, Fujinomiya (JP); Koichiro Furukawa, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 329 days.

(21) Appl. No.: 14/956,079

(22) Filed: Dec. 1, 2015

(65) Prior Publication Data
US 2016/0089499 A1 Mar. 31, 2016

Related U.S. Application Data

(63) Continuation of application No. PCT/JP2013/065697, filed on Jun. 6, 2013.

(51) Int. Cl.
*A61M 5/315* (2006.01)
*A61M 5/31* (2006.01)

(52) U.S. Cl.
CPC ...... *A61M 5/31513* (2013.01); *A61M 5/3129* (2013.01); *A61M 5/3134* (2013.01); *A61M 5/31515* (2013.01); *A61M 2005/3104* (2013.01); *A61M 2005/3131* (2013.01)

(58) Field of Classification Search
CPC .......... A61M 5/31515; A61M 5/31513; A61M 5/3129; A61M 5/3134; A61M 2005/3104; A61M 2005/3131
See application file for complete search history.

(56) References Cited

U.S. PATENT DOCUMENTS

| 9,101,720 B2 | 8/2015 | Okihara et al. |
| 2005/0010175 A1 | 1/2005 | Beedon et al. |

(Continued)

FOREIGN PATENT DOCUMENTS

| JP | 2003-245350 A | 9/2003 |
| JP | 2005-152183 A | 6/2005 |

(Continued)

OTHER PUBLICATIONS

Extended European Search Report and Search Opinion issued in European Patent Application No. 13886432.7 dated Nov. 10, 2016.

(Continued)

*Primary Examiner* — Lauren P Farrar
(74) *Attorney, Agent, or Firm* — Foley & Lardner LLP

(57) ABSTRACT

A syringe includes a gasket, a barrel, and a plunger. The plunger includes a helical rib provided on an outer surface of a head portion, and the gasket comprises a helical valley portion for threadedly engaging with the helical rib, a plunger-retaining annular rib, and an accommodation portion for a part of the plunger at which the helical rib is formed. The annular rib comprises a rib absent portion for guiding, to the accommodation portion, the helical rib reaching the annular rib as threaded engagement is advanced between the plunger and the gasket. The helical rib comprises an entrance-restricting terminal end portion for restricting the entrance of the helical rib into the rib absent portion after the part of the plunger 4 at which the helical rib is formed is stored in the accommodation portion 32 of the gasket.

11 Claims, 15 Drawing Sheets

(56) References Cited

U.S. PATENT DOCUMENTS

| 2011/0034882 A1* | 2/2011 | Quinn | A61M 5/31511 |
| | | | 604/218 |
| 2012/0184920 A1* | 7/2012 | Okihara | A61M 5/1452 |
| | | | 604/222 |
| 2016/0082194 A1 | 3/2016 | Furukawa | |

FOREIGN PATENT DOCUMENTS

| JP | 2007-202822 A | 8/2007 |
| JP | 2009-142508 A | 7/2009 |
| JP | 2011-072394 A | 4/2011 |
| JP | 2012-205931 A | 10/2012 |
| JP | 2014-196057 A1 | 2/2017 |
| WO | WO-2001/097885 A1 | 12/2001 |
| WO | WO-2004/075958 A2 | 9/2004 |
| WO | WO-2009/128265 A1 | 10/2009 |
| WO | WO-2011/040522 A1 | 4/2011 |

OTHER PUBLICATIONS

Notification of Reasons for Refusal with English Translation dated Feb. 28, 2017 in corresponding Japanese Patent Application No. 2015-521234.

International Search Report issued in PCT/JP2013/065697 dated Aug. 13, 2013.

* cited by examiner

SYRINGE AND PREFILLED SYRINGE

CROSS-REFERENCE TO RELATED PATENT APPLICATION

The present application is a continuation application of and claims the benefit of priority from International Patent Application No. PCT/JP2013/065697, filed Jun. 6, 2013, the contents of which are incorporated herein by reference in its entirety.

TECHNICAL FIELD

The present disclosure relates to a syringe, and a syringe that is prefilled with a liquid medicine.

BACKGROUND

Recent years, syringes have been frequently used in which a liquid, such as a liquid medicine, is prefilled in the syringe. Such prefilled syringes may be filled with a solvent for solving a medicine in a vial.

For insertion of a gasket into the prefilled syringe, a method called vacuum capping is generally used. In the method, a barrel comprising a sealed distal end opening is filled with a medicine, the gasket is disposed at an opening portion of the barrel in a reduced-pressure atmosphere (vacuum atmosphere), and then the gasket is inserted into the barrel upon increasing the reduced-pressure atmosphere to a normal pressure state. When a plunger is mounted to the gasket, it is difficult to mount the gasket to the opening portion of the barrel. Accordingly, the capping work is performed on the gasket without the plunger. Therefore, the prefilled syringe generally requires subsequent mounting of the plunger. For easy mounting of the plunger to the gasket, prevention of liquid leakage during mounting of the plunger, and inhibition of internal pressure rise, a mounting mechanism has been generally employed in which the plunger is provided with an external threaded portion and the gasket is provided with an internal threaded portion, and the plunger and the gasket are mounted to each other by threaded engagement.

As described above, in the prefilled syringe filled with the solvent, the plunger mounted to the gasket is operated to be drawn for dissolving the medicine in the vial in the solvent or recovering the dissolved medicine. However, when the plunger is drawn, there is a risk that the plunger may be separated from the gasket, and the medicine cannot be dissolved or the dissolved medicine cannot be recovered.

Prefilled syringes that have a mechanism for preventing such separation of the gasket are disclosed in Japanese Patent Application Publication No. 2009-142508 A ("Patent Literature 1") and Japanese Patent Application Publication No. 2011-72394 A ("Patent Literature 2"). It is noted that both Patent Literature 1 and Patent Literature 2 have been proposed by the applicant of the present application.

A syringe 10 of Patent Literature 1 comprises a gasket 3, a barrel 2, and a plunger 4. The plunger 4 comprises a helical rib 44 provided on an outer surface of a head portion 42, and the gasket comprises a helical valley portion 33 threadedly engaging with the helical rib, a plunger-retaining annular rib 34 positioned on the distal side near the helical valley portion 33, and an accommodation portion 32 for a part of the head portion of the plunger at which the helical rib is formed. The annular rib 34 comprises a rib absent portion 35 for guiding, to the accommodation portion, the helical rib reaching the annular rib as threaded engagement is advanced between the helical rib of the plunger and the helical valley portion of the gasket. The annular rib 34 prevents removal of the plunger from the gasket, retaining the helical rib 44 in the accommodation portion 32. A syringe 10 of Patent Literature 2 comprises a gasket 3, a barrel, and a plunger. The plunger comprises a helical rib provided at a head portion, and the gasket comprises a helical valley portion for threaded engagement with the helical rib, and an accommodation portion 32 for a part of the head portion of the plunger at which the helical rib is formed. The helical valley portion comprises helical crest portions 36, helical valley portions 33 formed between the helical crest portions 36, and a plunger retaining protrusion portion 34 formed at a terminal end part of the helical valley portion 33 and gradually protruding toward the accommodation portion 32. The protrusion portion 34 makes entrance of the helical rib of the plunger 4 into the terminal end part of the helical valley portion 33 difficult when the plunger is turned backward after being mounted to the gasket, and the protrusion portion 34 effectively prevents removal of the plunger from the gasket.

SUMMARY

In the syringes disclosed in Patent Literatures 1 and 2, the plungers are unlikely to be separated from the gaskets during normal operation, but when the plunger is turned while being strongly drawn proximally, the terminal end of the helical rib may enter the absent portion of the retaining annular rib.

It is an object of certain embodiments of the present invention to provide a syringe that is configured to readily mount a plunger to a gasket and is less likely to separate the gasket from the plunger after the gasket is mounted to the plunger, and a prefilled syringe using the syringe.

In one embodiment, a syringe includes a cylindrically-shaped gasket having a closed distal end and an opened proximal end. The gasket further includes an inner cavity portion extending distally from a proximal side, a barrel comprising a distal opening portion, the barrel being configured to store the gasket slidably, and a plunger comprising a head portion configured to be stored in the inner cavity portion of the gasket. The plunger includes a helical rib provided at the head portion, and comprises a starting end on a distal side and a terminal end on a proximal side. The gasket includes, on an inner surface of the inner cavity portion, a helical crest portion forming a helical valley portion threadedly engaging with the helical rib of the plunger, and a plunger-retaining annular rib positioned distally from the helical crest portion. The inner cavity portion includes an accommodation portion positioned distally from the retaining annular rib, the accommodation portion being configured to store a part of the head portion of the plunger at which the helical rib is formed. The retaining annular rib includes a rib absent portion for guiding, to the accommodation portion, the helical rib reaching the retaining annular rib as threaded engagement is advanced between the plunger and the gasket. The plunger includes, at the terminal end of the helical rib, an entrance-restricting terminal end portion for restricting the entrance of the helical rib into the rib absent portion, after storage of the part of the plunger at which the helical rib is formed, in the accommodation portion of the gasket.

In another embodiment, a syringe includes a cylindrically-shaped gasket having a closed distal end and an opened proximal end, and an inner cavity portion extending distally from a proximal side. The syringe further includes a barrel having a distal opening portion and configured to slidably store the gasket, and a plunger having a head portion configured to be stored in the inner cavity portion of the gasket. The plunger further includes a helical rib provided at the head portion, the helical rib having a starting end on a distal side and a terminal end on a proximal side. The gasket includes, on an inner surface of the inner cavity portion, a helical crest portion forming a helical valley portion threadedly engaging with the helical rib of the plunger, and an accommodation portion positioned distally from the helical crest portion, the accommodation portion configured to store the part of the head portion of the plunger at which the helical rib is formed. The helical valley portion includes a proximal end near an opening portion of the inner cavity portion, distally extending by a predetermined length, and a terminal end positioned proximally from the accommodation portion. The plunger includes, at the terminal end of the helical rib, an entrance-restricting terminal end portion for restricting the entrance of the helical rib into the terminal end of the helical valley portion, after storage of a part of the plunger at which the helical rib is formed, in the accommodation portion of the gasket.

A prefilled syringe comprising a syringe according to any of the above embodiments, a sealing member for sealing a distal opening portion of the barrel, and a medicine stored in the barrel.

DESCRIPTION OF THE EMBODIMENTS

Figure 1:
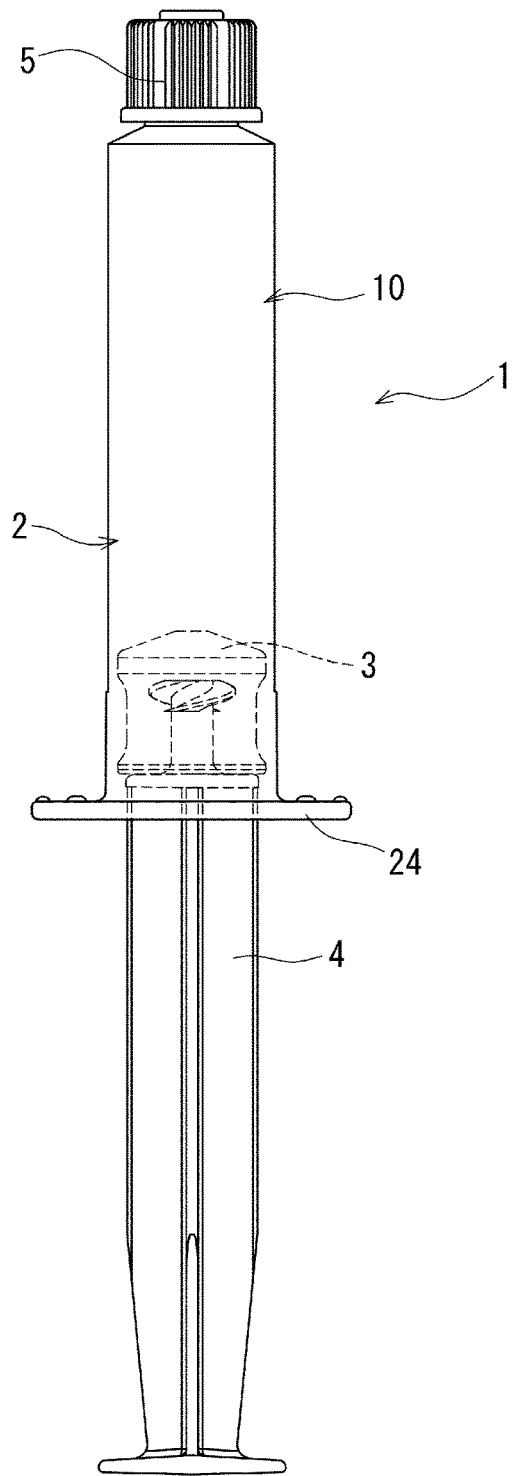
FIG. 1 is a front view of a prefilled syringe using a syringe according to a first embodiment of the present invention.

A syringe and a prefilled syringe according to the present invention will be described below using an embodiment illustrated in the drawings.

Figure 2:
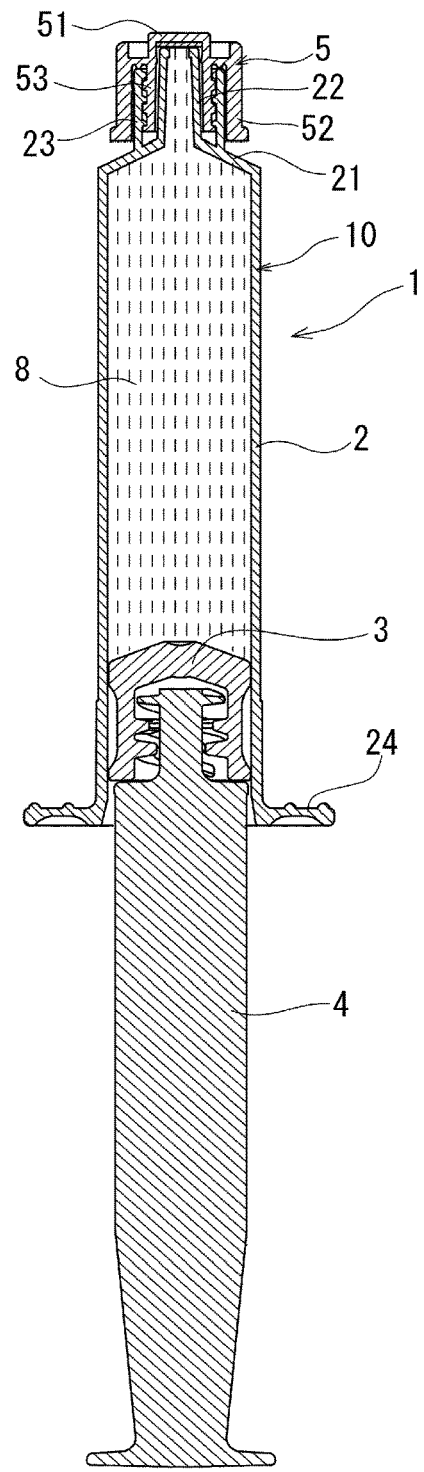
FIG. 2 is a vertical cross-sectional view of the prefilled syringe illustrated in FIG. 1.
Figure 4:
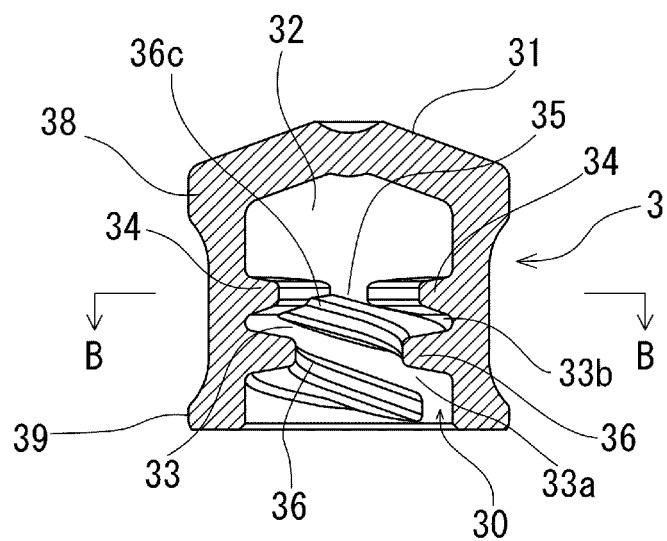
FIG. 4 is a cross-sectional view taken along the line A-A of FIG. 3.

As illustrated in FIGS. 1 and 2, the syringe 10 includes a gasket 3 being a cylindrical body. The gasket 3 has a closed distal end and an opened proximal end, and includes an inner cavity portion 30 extending distally from a proximal side, as illustrated in FIG. 4. The syringe 10 further includes a barrel 2, which includes a distal opening portion and slidably stores the gasket 3, as illustrated in FIG. 2, and a plunger 4, which includes a head portion 42 stored in the inner cavity portion 30 of the gasket 3, as illustrated in FIG. 6.

Figure 6:
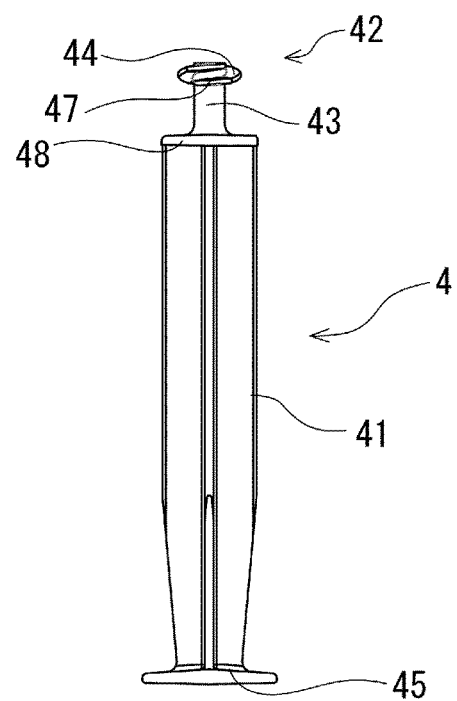
FIG. 6 is a front view of a plunger used for a syringe according to the first embodiment of the present invention.

As illustrated in FIG. 6, the plunger 4 includes helical ribs 44 provided at the head portion 42. Each of the helical ribs 44 includes a starting end on a distal side and a terminal end on a proximal side.

Figure 8:
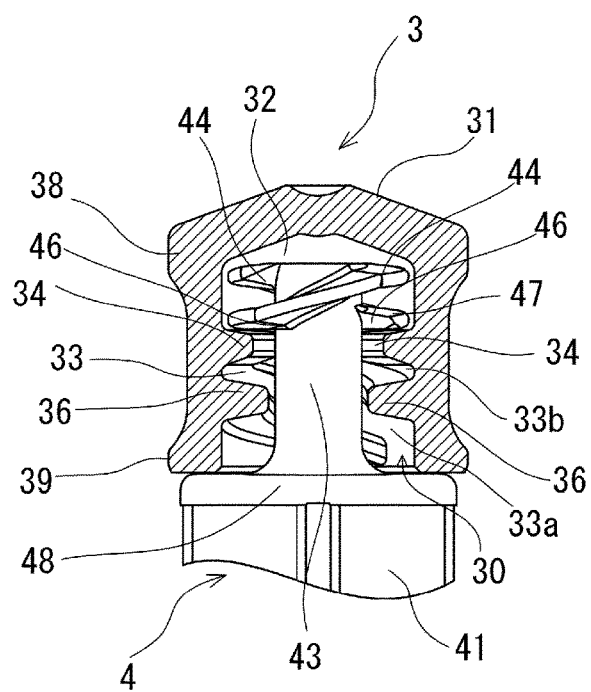
FIG. 8 is a schematic diagram illustrating an effect upon mounting a gasket and a plunger in a syringe according to the first embodiment of the present invention.

As illustrated in FIG. 8, the gasket 3 comprises, on an inner surface of the inner cavity portion 30, helical crest portions 36 forming helical valley portions 33 for threadedly engaging with the helical ribs 44 of the plunger 4 and a plunger-retaining annular rib 34 positioned distally from the helical crest portions 36. The inner cavity portion 30 also includes an accommodation portion 32 positioned distally from the annular rib 34, which is configured to store a part of the head portion 42 of the plunger 4 at which the helical ribs are formed. As shown in FIG. 4, the plunger-retaining annular rib 34 has a rib absent portion 35 for guiding, to the accommodation portion 32, a helical rib 44 reaching the plunger-retaining annular rib 34 as threaded engagement is advanced between the helical rib 44 of the head portion 42 of the plunger 4 and the helical valley portions 33 of the gasket 3.

The plunger 4 includes, at the terminal end of the helical rib 44, an entrance-restricting terminal end portion 46 for restricting the entrance of the helical rib 44 into the rib absent portion 35, after storage of the part of the plunger 4 at which the helical ribs are formed in the accommodation portion 32 of the gasket 3.

In this syringe, after the plunger is mounted to the gasket, even if the plunger is turned in a direction (unthreading direction) opposite to the threading direction between the gasket and the plunger while the plunger is drawn proximally, the plunger slips, and the proximal side of the helical rib of the plunger does not enter the absent portion of the retaining annular rib. Therefore, the plunger is prevented from being separated from the gasket.

Figure 3:
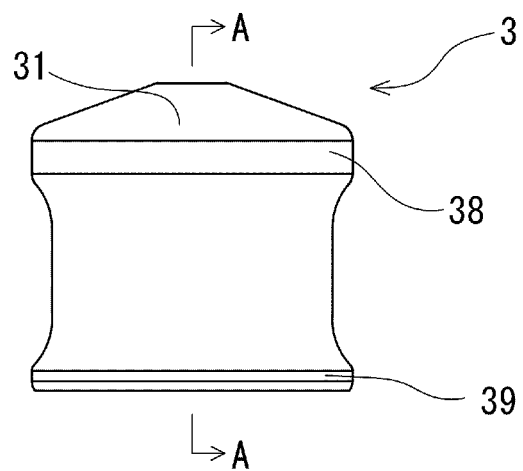
FIG. 3 is an enlarged front view of a gasket used for a syringe according to the first embodiment of the present invention.

Further, as illustrated in FIGS. 1 and 2, the prefilled syringe 1 according to the present invention comprises the syringe 10 for the prefilled syringe, a sealing member 5 for sealing the distal opening portion of the barrel 2, and a medicine 8 stored in the barrel 2. The syringe 10 according to the present example comprises the barrel 2, the gasket 3 slidably stored in the barrel, and the plunger 4 mounted to or being mountable to the gasket 3. The prefilled syringe 1 comprises the syringe 10, the sealing member 5 for sealing the distal opening portion of the barrel 2, and the medicine 8 stored in the syringe (in the barrel). As illustrated in FIGS. 1 to 5, the gasket 3 according to the present example is a cylindrical body comprising the closed distal end, and the inner cavity portion 30 extending distally from a proximal end opening. As illustrated in FIGS. 3 and 4, the gasket 3 comprises, at a distal part, a tapered portion 31 having a diameter reduced in a tapered manner toward the distal side.

The gasket 3 for the syringe comprises the inner cavity portion 30, and the inner cavity portion 30 comprises a plunger-mounting function. The inner cavity portion 30 comprises, on the inner surface, the helical crest portions 36 forming the helical valley portions 33 for threadedly engaging with the helical rib 44 of the plunger 4, and the plunger-retaining annular rib 34 positioned on the distal side near the helical crest portions 36 (helical valley portions 33). Further, the inner cavity portion 30 comprises the accommodation portion 32 positioned distally from the retaining annular rib 34, and configured to accommodate the part of the head portion 42 of the plunger 4 at which the helical ribs are formed. The retaining annular rib 34 comprises the rib absent portion 35 for guiding, to the accommodation portion 32, the helical rib 44 reaching the retaining annular rib 34 as threaded engagement is advanced between the helical rib 44 of the head portion 42 of the plunger 4 and the helical valley portion 33 of the gasket 3.

Figure 5:
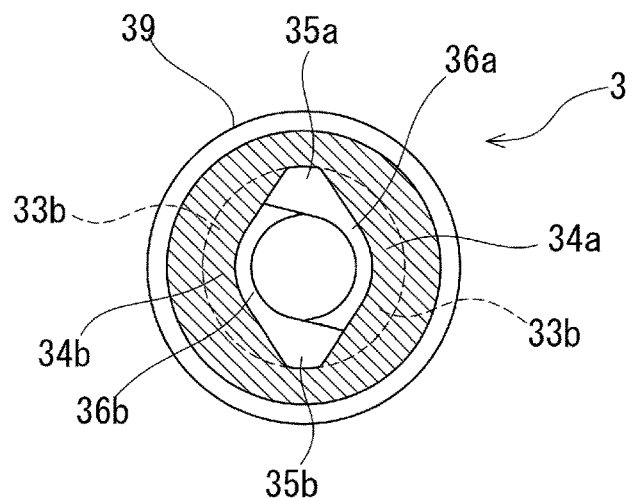
FIG. 5 is a cross-sectional view taken along the line B-B of FIG. 4.

A helical valley portion (threaded engagement portion) 33 includes a proximal end 33a near the opening portion of the inner cavity portion 30 and distally extends by a predetermined length to a distal end 33b near the rib absent portion 35 of the retaining annular rib 34. In the present example, the helical valley portions 33 are formed to have two helical valley portions 33 to correspond to the helical ribs 44 of the head portion 42 of the plunger 4 described below. The gasket 3 according to the present example comprises two helical crest portions 36a and 36b to form two helical valley portions, as illustrated in FIGS. 4 and 5. Although a plurality of (specifically, two) helical valley portions as described above is preferably provided, only one helical crest portion (helical crest portion) may be provided.

Further, in the present example, the helical valley portion 33 is formed as a groove-shaped portion formed between the helical crest portions 36 projecting from an inner wall surface of the inner cavity portion 30 of the gasket 3. The helical valley portion 33 is configured to threadedly engage with the helical rib 44 of the plunger 4 to distally guide the helical rib 44.

The gasket 3 comprises the plunger-retaining annular rib 34 provided on an inner surface of a part positioned near the helical valley portion 33, and distally from the helical valley portion 33. In the gasket according to the present example, the retaining annular rib 34 is configured to extend in a direction substantially perpendicular to an axis of the gasket 3. However, the retaining annular rib 34 preferably extends in a direction perpendicular to the axis of the gasket 3, but may be slightly oblique to the perpendicular state. Further, the gasket 3 comprises the accommodation portion 32 positioned distally from the retaining annular rib 34, and configured to accommodate the part of the head portion 42 of the plunger 4 at which the helical ribs are formed.

Further the retaining annular rib 34 comprises the rib absent portion 35 for guiding, to the accommodation portion 32, the helical rib 44 reaching the retaining annular rib 34 as threaded engagement is advanced between the helical rib 44 of the head portion 42 of the plunger 4 and the helical valley portion 33 of the gasket 3. In particular, in the gasket 3 according to the present example, the helical valley portion 33 is formed as two helical valley portions corresponding to the two helical ribs, as described above, and the annular rib comprises two absent portions provided at substantially opposed positions corresponding to two helical valley portions, as illustrated in FIG. 5. In other words, the gasket 3 comprises two retaining annular ribs 34a and 34b, and the two rib absent portions 35a and 35b positioned between the two retaining annular ribs 34a and 34b. Further, as illustrated in FIG. 5, the retaining annular rib 34 (34a, 34b) preferably comprises a rib (projection height) gradually reduced toward the rib absent portion 35 (35a, 35b). It is noted that the retaining annular rib 34 (34a, 34b) may have a width that is gradually reduced, a height that is gradually reduced, or a width that is gradually reduced and a height that is gradually reduced toward the rib absent portion 35 (35a, 35b). As the retaining annular rib 34 is configured as described above, passage of the helical rib 44 of the plunger 4 through the retaining annular rib 34, i.e., entrance of the helical rib 44 of the plunger 4 into the accommodation portion 32, is further facilitated. It is noted that in the rib absent portion, even if the retaining annular rib is not completely absent, the retaining annular rib is preferably partially absent to guide the helical rib of the head portion.

In the gasket 3 according to the present example, a proximal end of a helical crest portion 36 is positioned near the opening portion of the inner cavity portion 32, and a distal end 36c of the helical crest portion 36 is connected to a part of the retaining annular rib 34 adjacent to the rib absent portion 35. In other words, the distal end 36c of the helical crest portion 36 is connected to a proximal side surface of one end of the retaining annular rib 34 formed by the rib absent portion 35. Further, a surface on the distal side of the distal end part of the helical crest portion 36 is adjacent to a proximal end of the rib absent portion 35. In other words, the surface on the distal side of the distal end part of the helical crest portion 36 is positioned close to the rib absent portion 35, on the proximal side. Therefore, the starting end of the helical rib 44 is surely guided to the rib absent portion 35. Further, the helical rib 44 can pass through the rib absent portion 35 and ride over the retaining annular rib 34 without considerably deforming the retaining annular rib 34 near the rib absent portion 35.

As illustrated in FIG. 4, a distance between the helical crest portion 36 and the retaining annular rib 34 is configured to be reduced toward the rib absent portion 35 (similarly, toward the distal end 33b of the helical valley portion 33). Therefore, the helical rib 44 of the plunger 4 is surely guided to the rib absent portion 35 of the retaining annular rib 34. Further, the helical crest portion 36 for forming the helical valley portion 33 of the gasket 3 preferably comprises a projection height higher than a projection height of the retaining annular rib 34. This is because threaded engagement between the helical crest portion 36 and the helical rib 44 is readily maintained in order to surely pass the helical rib 44 of the plunger 4 to be turned, through the rib absent portion 35 of the retaining annular rib 34 to store the part at which the helical ribs 44 are formed in the accommodation portion 32, upon mounting the plunger 4 to the gasket 3.

Although the height (inward projection length) of the retaining annular rib 34 is different depending on the size or hardness of the gasket, the height is preferably 0.5 to 2.0 mm, in particular 0.8 to 1.5 mm. Further, the width of the rib absent portion 35 of the retaining annular rib 34 in a circumferential direction of the gasket 3 is preferably 0.5 to 3.0 mm, in particular 0.5 to 1.5 mm.

Further, the gasket 3 comprises a small projection portion projecting toward the proximal side at a center part of an inner surface of a distal end part. The projection portion is configured to abut on a distal end part of the head portion of the plunger 3 upon proximal deformation of the distal end of the gasket 3, and excessive deformation of a distal end part of the gasket 3 is prevented. The projection portion preferably comprises a substantially semi-spherical shape. Generally, the gasket 3 comprises a diameter of 5 to 30 mm, and a total length of approximately 5 to 30 mm.

The gasket 3 comprises, on an outer peripheral surface, a distal side annular rib 38 having an outer diameter larger than an inner diameter of the barrel 2, and a proximal side annular rib 39 similarly having an outer diameter larger than the inner diameter of the barrel 2. The distal side annular rib 38 is provided on an outer surface of a distal end of a cylindrical main body portion, and the proximal side annular rib 39 is provided on a proximal outer surface of the main body portion.

The distal side annular rib 38 is provided on the outer surface of the distal end of the cylindrical main body portion, and the proximal side annular rib 39 is provided on the proximal outer surface of the main body portion. The distal side annular rib 38 and the proximal side annular rib 39 preferably have an outer diameter larger than the inner diameter of the barrel 2 by 0.5 to 1.5 mm and, in particular, when the inner diameter of the barrel 2 is 8 to 10 mm, the outer diameters are preferably larger than the inner diameter of the barrel 2 by 0.5 to 0.8 mm. Therefore, while maintaining liquid tightness between the gasket 3 and an inner peripheral surface of the barrel 2, sliding resistance of the gasket 3 sliding in the barrel 2 can be reduced. Further, the distal side annular rib 38 and the proximal side annular rib 39 each have an outermost projecting top part extending linearly in the axial direction of the gasket 3. The top part of the distal side annular rib 38 is preferably formed to have a large width in the axial direction, as illustrated in FIG. 3. The top part of the distal side annular rib 38 preferably has an axial length longer than an axial length of the proximal side annular rib 39. The axial length of the distal side annular rib 38 is preferably 0.8 to 2 mm, in particular 0.8 to 1.5 mm. The axial length of the proximal side annular rib 39 is preferably 0.1 to 1.0 mm, in particular 0.2 to 0.5 mm. Owing to the configuration as described above, a contact area between the gasket 3 and the inner peripheral surface of the barrel 2 is increased, and the liquid tightness is increased and the liquid medicine is not likely to leak.

As a component material of the gasket 3, a known material conventionally used for gaskets can be employed. The material includes, for example, a rubber, an elastomer, a polyolefin-based resin, a fluorine-based resin, or a polyester-based resin. The rubber preferably includes, for example, a natural rubber, isoprene rubber, butyl rubber, chloroprene rubber, nitrile-butadiene rubber, styrene-butadiene rubber, or silicone rubber, especially a vulcanized rubber. The elastomer preferably includes, for example, a polyvinyl chloride-based elastomer, a polyolefin-based elastomer, a styrene-based elastomer, a polyester-based elastomer, a polyamide-based elastomer, a polyurethane-based elastomer, or a mixture thereof. Especially, styrene-butadiene rubber, butyl rubber, or styrene-based elastomer is preferably selected from the above-mentioned rubbers and elastomers. The styrene-butadiene rubber, butyl rubber, and styrene-based elastomer have a preferred hardness and elastic property and can be adapted for a sterilization method, such as γ-sterilization, electron-beam sterilization, or high-pressure steam sterilization.

Further, a distal side of the gasket may be coated with a low medicine-adsorbing material or the like. As a material of a low medicine-adsorbing layer, a known material conventionally used for laminate gaskets can be used. The material of the low medicine-adsorbing layer includes, for example, a polyolefin-based resin, a fluorine-based resin, or a polyester-based resin. Specifically, the polyolefin-based resin preferably includes a polypropylene, an ultrahigh molecular weight polyethylene, a poly(4-methylpentene-1), a cyclic polyolefin, or the like. The fluorine-based resin preferably includes a tetrafluoroethylene-perfluoroethoxyethylene copolymer, a polytetrafluoroethylene, a tetrafluoroethylene/perfluoro(alkyl vinyl ether) copolymer, a tetrafluoroethylene/hexafluoropropylene copolymer, or the like. Further an outer surface of the gasket 3, or at least surfaces of the distal side annular rib 38 and the proximal side annular rib 39 are preferably coated with a lubricant agent. As the lubricant agent, a silicone oil is preferably employed.

As illustrated in FIG. 1, FIG. 2, and FIGS. 6 to 8, the plunger 4 comprises a plunger body portion 41 and the head portion 42 projecting distally from the plunger body portion 41. The plunger body portion 41 comprises a disk portion 48 positioned at a distal end and the head portion 42 projecting therefrom, and a pressing portion 45 positioned at a proximal end. As illustrated in FIGS. 6 and 8, the plunger body portion 41 comprises a shaft portion comprising a cross-shaped cross-section, the shaft portion is provided with the disk portion 48 at a distal end thereof and the pressing portion 45 for the plunger, which has a disk-shape on a proximal side.

Figure 7:
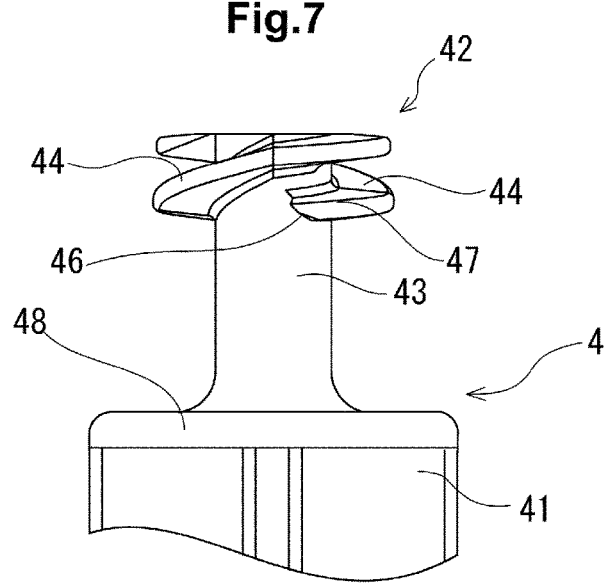
FIG. 7 is an enlarged right side view of a distal end part of the plunger illustrated in FIG. 6.

The head portion 42 is a projection portion provided at a distal end part of the plunger 4. The head portion 42 projects forward from near the center of the disk portion 48 provided at the distal end of the body portion 41. The head portion 42 is configured to have a rod shape. As illustrated in FIGS. 6 to 8, the head portion 42 comprises a shaft portion 43, and the helical rib 44 formed on an outer surface of the shaft portion 43. Further, the shaft portion 43 comprises a flat distal end. The shaft portion 43 may have a cylindrical shape or a columnar shape, and may have a cross-section of polygonal shape such as a square, pentagonal, hexagonal cross-section, or a cruciform.

The helical rib 44 is formed on an outer surface of a distal end of the head portion 42 of the plunger 4, in particular, on an outer surface of a distal end of the shaft portion 43. As illustrated in FIGS. 6 to 8, in the plunger 4 according to the present example, two helical ribs 44 are formed corresponding to the above-mentioned helical valley portions 33 of the gasket 3. The helical rib 44 is configured to have a starting end at the distal end part of the head portion 42 of the plunger 4, specifically at the distal end of the shaft portion 43, proximally extends by a predetermined length, and comprises a terminal end on a proximal side. Although a plurality of (specifically, two) helical ribs as described above is preferably provided, only one helical rib may be provided.

The helical rib 44 of the plunger 4 preferably has a height (outward projection length) of 0.5 to 2.5 mm, in particular, 1.0 to 2.0 mm. As a component material of the plunger 4, a hard or semi-hard resin, such as a high-density polyethylene, a polypropylene, a polystyrene, a polyethylene terephthalate, is preferably used.

The helical rib 44 comprises the entrance-restricting terminal end portion 46 for restricting the entrance of the helical rib 44 into the rib absent portion 35, after storage of the part of the plunger 4 at which the helical ribs are formed in the accommodation portion 32 of the gasket 3.

Especially, in the plunger 4 according to an example illustrated in FIGS. 6 to 8, the entrance-restricting terminal end portion 46 of the helical rib 44 comprises an inclined terminal end surface 46 for entrance restriction. The inclined terminal end surface 46 is formed at the terminal end of the helical rib 44, and is positioned obliquely by a predetermined angle to the axis of the shaft portion to extend a surface on the distal side of the helical rib 44 longer in the circumferential direction of the shaft portion than a surface on the proximal side of the helical rib 44.

Specifically, as illustrated in FIGS. 7 and 8, the inclined terminal end surface 46 is configured to be directed obliquely by the predetermined angle to the axis of the shaft portion 43 of the plunger 4 toward the proximal end. Therefore, the proximal side of the helical rib 44 is configured to have the surface on the distal side directed toward the distal end of the plunger 4, the surface on the proximal side directed toward the proximal end (disk portion 48) of the plunger 4, and the inclined terminal end surface 46 being an inclined surface connecting the surface on the distal side and the surface on the proximal side, and directed obliquely toward the proximal end.

The inclined terminal end surface 46 preferably has an inclination angle to the axis of the shaft portion 43 of the plunger 4 of 30 to 60 degrees, in particular 40 to 70 degrees.

When the plunger 4 is turned in a direction opposite to the thread engaging direction, the inclined terminal end surface 46 of the helical rib 44 is defined as a distal part for entrance of the annular rib 34 into the rib absent portion 35. Since the inclined terminal end surface 46 as described above is provided at the terminal end of the helical rib 44, even if the helical ribs 44 are turned backward, the inclined terminal end surface 46 abuts on a side surface of a part of the helical crest portion 36 adjacent to the rib absent portion 35, and the terminal end of the helical rib 44 is not likely to enter the helical valley portion 33 from the rib absent portion 35. Further, since the inclined terminal end surface 46 is an inclined surface directed obliquely toward the proximal end, when the inclined terminal end surface 46 abuts on the side surface of the part of the helical crest portion 36 adjacent to the rib absent portion 35, a force directed obliquely toward the distal end is generated in the helical rib 44. Therefore, the plunger 4 readily slips, and the plunger 4 is not likely to be removed from the gasket 3.

Further, in the plunger 4 according to the present example, the helical rib 44 comprises a helix terminal end portion 47 (circumferentially extending portion) having a helical inclination smaller than that of a part on the distal side of the helical rib 44. The helix terminal end portion is inclined considerably gently toward the terminal end. Accordingly, the helix terminal end portion 47 comprises a proximal end surface configured to be almost perpendicular to the axis of the shaft portion 43. The helix terminal end portion 47 having such a small inclination is provided to have a distance between the surface on the distal side of the terminal end portion 47 of the helical rib 44 and the surface on the proximal side of the helical rib 44 facing the surface on the distal side of the terminal end portion 47 in a distal direction is smaller than the distance in any other part of the helical rib. Therefore, when the plunger 4 mounted to the gasket 3 is turned, the terminal end of the helical rib 44 is not likely to enter the helical valley portion 33 from the rib absent portion 35. The helix terminal end portion 47 preferably has a center angle of 30 to 150 degrees, in particular 80 to 100 degrees. It is noted that, here, the center angle of the helix terminal end portion 47 (circumferentially extending portion) represents an angle between two straight lines connecting the axis of the shaft portion and the starting end and the terminal end of the helix terminal end portion (circumferentially extending portion), respectively.

In the gasket 3, the plunger 4 is configured so that after the helical rib 44 of the plunger 4 is inserted into the proximal end of the helical valley portion 33 of the gasket 3, the plunger 4 is turned to advance the threaded engagement between the helical rib 44 and the helical valley portion 33. When the plunger 4 is further turned, the helical rib 44 passes through the rib absent portion 35 of the retaining annular rib 34 to enter the accommodation portion 32. When the plunger keeps turning, the whole of the helical rib 44 passes through the rib absent portion 35 of the retaining annular rib 34, and the part of the head portion 42 of the plunger 4 at which the helical ribs are formed is stored in the accommodation portion 32 of the gasket 3, as illustrated in FIG. 8.

While the plunger 4 is mounted to the gasket 3, the proximal end surface of the helical rib 44 (helix terminal end portion 47) of the plunger 4 abuts on a distal end surface of the retaining annular rib 34 of the gasket 3, and the separation of the plunger 4 from the gasket 3 is restricted. Further, in the plunger 4, the helical rib 44 comprises the helix terminal end portion 47 (circumferentially extending portion) at the proximal end. Therefore, the proximal end surface of the helical rib 44 of the plunger 4 abutting on the distal end surface of the retaining annular rib 34 is increased in size, and separation of the plunger 4 from the gasket 3 is surely prevented when the plunger 4 is drawn proximally. Further in the plunger 4, the helical rib 44 comprises the inclined terminal end surface 46 at the terminal end. Therefore, when an operation that is not performed usually, such as turning the plunger 4 as it is drawn proximally, is performed, the inclined terminal end surface 46 abuts on the side surface of the part of the helical crest portion 36 adjacent to the rib absent portion 35, and the terminal end of the helical rib 44 is not likely to enter the helical valley portion 33 from the rib absent portion 35. Therefore, even if a special operation as described above is performed, separation of the plunger 4 from the gasket 3 is prevented.

Figure 11:
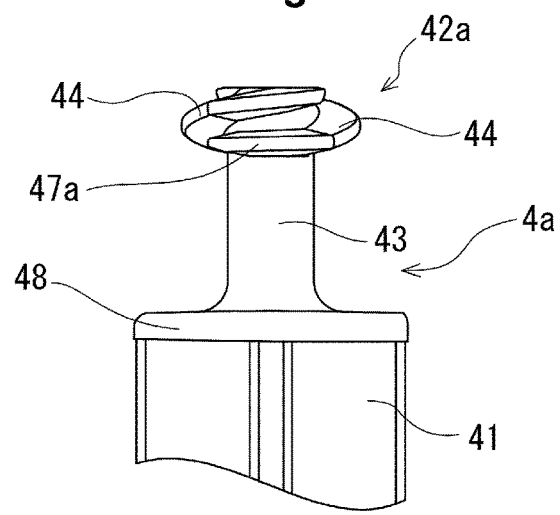
FIG. 11 is an enlarged front view of a distal end part of a plunger according to another example.
Figure 12:
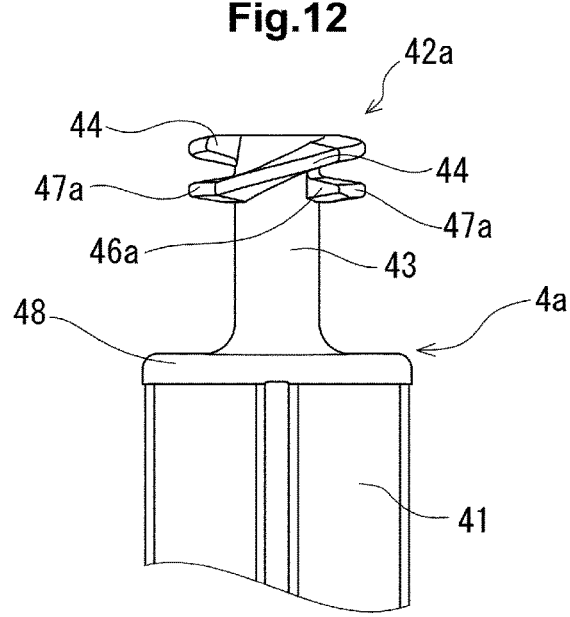
FIG. 12 is a right side view of the plunger illustrated in FIG. 11.
Figure 13:
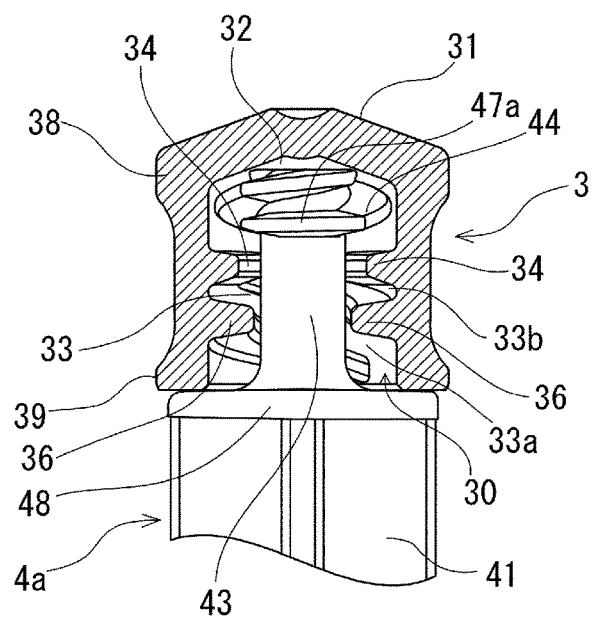
FIG. 13 is a schematic diagram illustrating an effect upon mounting a gasket and a plunger in a syringe using the plunger illustrated in FIGS. 11 and 12.

Further, the entrance-restricting terminal end portion of the helical rib 44 may be a type of a plunger 4a according to an example illustrated in FIGS. 11 to 13. In the present example, the entrance-restricting terminal end portion of the helical rib comprises a circumferentially extending portion 47a substantially perpendicular to the axis of the shaft portion 43, and extending by a predetermined length in the circumferential direction of the shaft portion 43.

Specifically, in the plunger 4a according to the present example, the helical rib 44 comprises the circumferentially extending portion 47a provided at the proximal end of the helical rib 44 and extending in the circumferential direction of the shaft portion 43. The circumferentially extending portion 47a extends by a predetermined length in the circumferential direction, substantially perpendicular to the axis of the shaft portion 43. Therefore, the terminal end part of the helical rib substantially does not have a helical form. The circumferentially extending portion 47a has a substantially flat proximal end surface. Therefore, while the plunger 4a is mounted to the gasket 3, the proximal end surface of the circumferentially extending portion 47a is substantially parallel to the annular rib 34 of the gasket 3.

Further, the circumferentially extending portion 47a is configured to pass through the helical valley portion 33 of the gasket 3 and the absent portion of the retaining annular rib 34. The center angle of the circumferentially extending portion 47a is preferably 30 to 150 degrees, in particular, 80 to 100 degrees.

Similar to the above-mentioned plunger 4, the plunger 4a is configured so that after the helical rib 44 of the plunger 4a is inserted into the proximal end of the helical valley portion 33 of the gasket 3, the plunger 4a is turned to advance the threaded engagement between the helical rib 44 and the helical valley portion 33. When the plunger 4a is further turned, the helical rib 44 passes through the rib absent portion 35 of the retaining annular rib 34 and enters the accommodation portion 32. When the plunger keeps turning, the whole of the helical rib 44 passes through the rib absent portion 35 of the retaining annular rib 34, and the part of the head portion 42a of the plunger 4a at which the helical ribs are formed is configured to be stored in the accommodation portion 32 of the gasket 3, as illustrated in FIG. 13.

While the plunger 4a is mounted to the gasket 3, the proximal end surface of the helical rib 44 of the plunger 4a abuts on the distal end surface of the retaining annular rib 34 of the gasket 3, and the separation of the plunger 4a from the gasket 3 is restricted. Further, in the plunger 4a according to the present example, the helical rib 44 comprises the circumferentially extending portion 47a at the proximal end. Therefore, the proximal end surface of the helical rib 44 of the plunger 4a abutting on the distal end surface of the retaining annular rib 34 is increased in size, and separation of the plunger 4a from the gasket 3 is surely prevented when the plunger 4a is drawn proximally. Further, in the present example, the circumferentially extending portion 47a has a terminal end surface formed as a rising terminal end surface 46a extending parallel to the axis of the shaft portion 43. When the plunger 4 is turned in a direction opposite to the thread engaging direction, the rising terminal end surface 46a of the helical rib 44 is defined as a distal end portion for entrance of the annular rib 34 into the rib absent portion 35. Since the rising terminal end surface 46a as described above is provided at the terminal end of the helical rib 44, even if the helical rib 44 is turned backward, the rising terminal end surface 46a abuts on the side surface of the part of the helical crest portion 36 adjacent to the rib absent portion 35, and the terminal end of the helical rib 44 is not likely to enter the helical valley portion 33 from the rib absent portion 35. Therefore, even if the special operation as described above is performed, separation of the plunger 4a from the gasket 3 is prevented.

Figure 14:
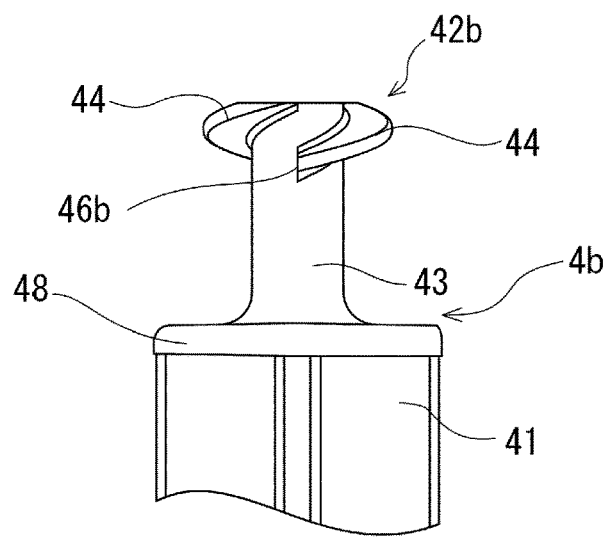
FIG. 14 is an enlarged front view of a distal end part of a plunger according to another example.
Figure 15:
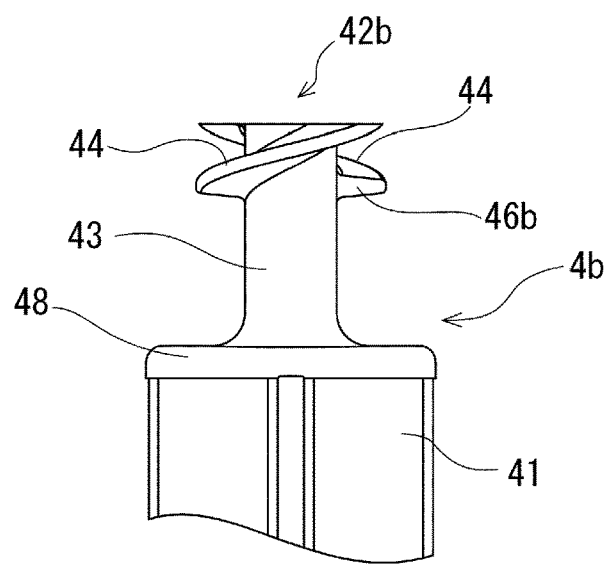
FIG. 15 is a right side view of the plunger illustrated in FIG. 14.
Figure 16:
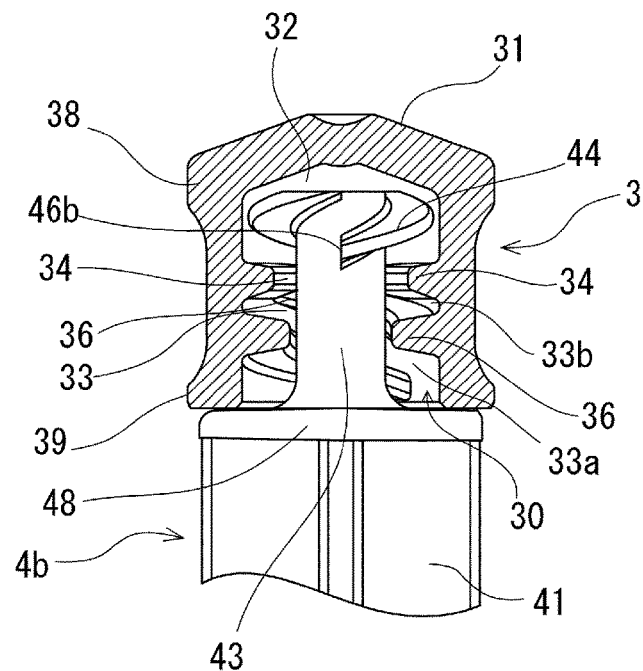
FIG. 16 is a schematic diagram illustrating an effect upon mounting a gasket and a plunger in a syringe using the plunger illustrated in FIGS. 14 and 15.

Further, the entrance-restricting terminal end portion of the helical rib 44 may be a type of a plunger 4b according to an example illustrated in FIGS. 14 to 16. In the present example, the helical rib has a certain inclination from the starting end to the terminal end, and the entrance-restricting terminal end portion of the helical rib comprises a rising terminal end surface 46b formed at the terminal end of the helical rib 44, and extending substantially parallel to the axis of the shaft portion 43.

As illustrated in FIGS. 14 and 16, the rising terminal end surface 46b is formed substantially parallel to the axis of the shaft portion 43. The helical rib 44 is formed to be gradually reduced in thickness toward the distal end (starting end), in the distal end part (starting end portion). However, in the proximal side, the helical rib is cut to the axis of the shaft portion 43. That is, the terminal end of the helical rib 44 is configured to have a thickness and a shape the same as those of parts other than the distal end part of the helical rib. Therefore, the rising terminal end surface 46b also has a sufficient area. Further, although the rising terminal end surface 46b has a thickness gradually reduced toward an outer end thereof, the rising terminal end surface 46b has a sufficient height (thickness) at the outer end. The rising terminal end surface 46b is preferably parallel to the axis of the shaft portion 43, but may be slightly oblique to the axis. In this configuration, the rising terminal end surface 46b is preferably inclined toward the proximal side (toward disk portion 48). Further, the rising terminal end surface 46b preferably comprises a flat surface, but may have an uneven surface or a curved surface.

Similar to the above-mentioned plunger 4, the plunger 4b is configured so that after the helical rib 44 of the plunger 4b is inserted into the proximal end of the helical valley portion 33 of the gasket 3, the plunger 4b is turned to advance the threaded engagement between the helical rib 44 and the helical valley portion 33. When the plunger 4b is further turned, the helical rib 44 passes through the rib absent portion 35 of the retaining annular rib 34 to enter the accommodation portion 32. When the plunger keeps turning, the whole of the helical rib 44 passes through the rib absent portion 35 of the retaining annular rib 34, and the part of the head portion 42b of the plunger 4b at which the helical ribs are formed is configured to be stored in the accommodation portion 32 of the gasket 3, as illustrated in FIG. 16.

While the plunger 4b is mounted to the gasket 3, the proximal end surface of the helical rib 44 of the plunger 4b abuts on the distal end surface of the retaining annular rib 34 of the gasket 3, and the separation of the plunger 4b from the gasket 3 is restricted. Further, in the plunger 4b according to the present example, the helical rib 44 comprises the rising terminal end surface 46b. When the plunger 4 is turned in a direction opposite to the thread engaging direction, the rising terminal end surface 46b of the helical rib 44 is defined as a distal end portion for entrance of the annular rib 34 into the rib absent portion 35. Since the rising terminal end surface 46b as described above is provided at the terminal end of the helical rib 44, even if the helical rib 44 is turned backward, the rising terminal end surface 46b abuts on the side surface of the part of the helical crest portion 36 adjacent to the rib absent portion 35, and the helical rib 44 is not likely to enter the rib absent portion 35. Therefore, even if the special operation as described above is performed, separation of the plunger 4b from the gasket 3 is prevented.

It is noted that in all of the examples having been described above, two helical ribs 44 are provided, and the terminal end of each helical rib 44 is provided with the entrance-restricting terminal end portion. Although such a configuration as described above is preferably employed, only one of the helical ribs 44 may be provided with the entrance-restricting terminal end portion.

Further, when the terminal end of each helical rib 44 is provided with the entrance-restricting terminal end portion, the entrance-restricting terminal end portion preferably has the same mode, but an arbitrary combination of the modes of the entrance-restricting terminal end portions in all of the above-mentioned examples may be employed.

Figure 17:
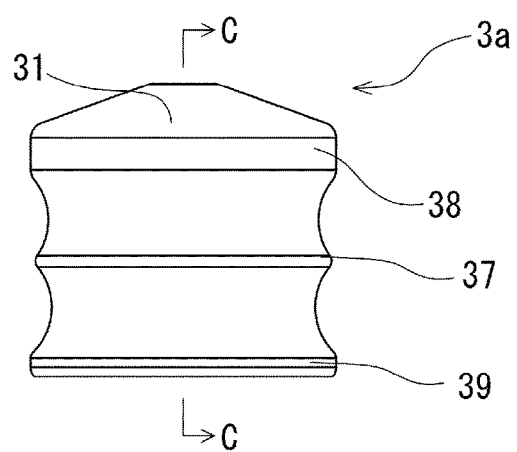
FIG. 17 is an enlarged front view of a gasket according to another example.
Figure 18:
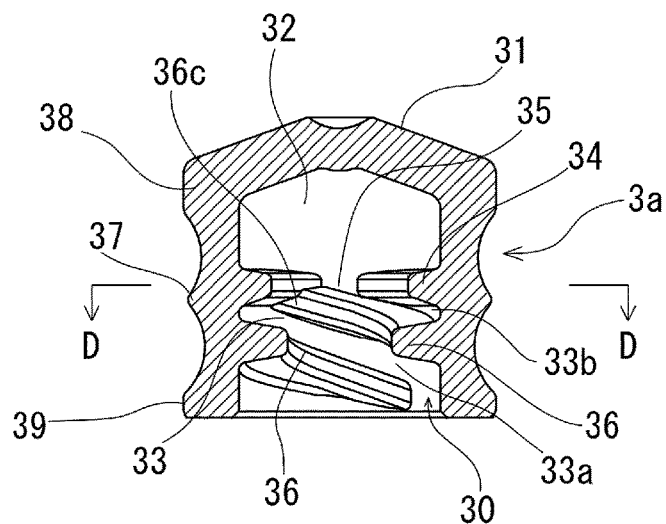
FIG. 18 is a cross-sectional view taken along the line C-C of FIG. 17.
Figure 19:
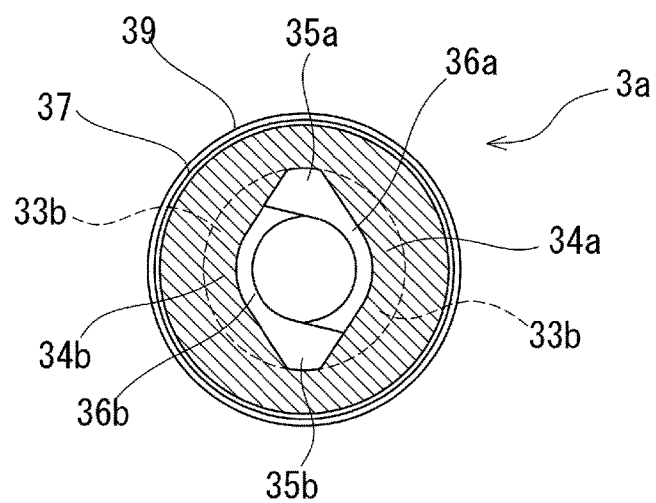
FIG. 19 is a cross-sectional view taken along the line D-D of FIG. 18.

In all of the examples having been described above, the outer peripheral surface of the gasket may comprise an intermediate annular rib 37 provided between the distal side annular rib 38 and the proximal side annular rib 39, as is in a case of a gasket 3a according to an example illustrated in FIGS. 17 to 19.

The intermediate annular rib 37 is provided on an outer peripheral surface of the gasket 3a, and is formed between the distal side annular rib 38 and the proximal side annular rib 39. The intermediate annular rib 37 is circumferentially provided along the outer peripheral surface of the gasket 3a, in a direction perpendicular to an axis of the gasket 3a. Further, as illustrated in FIGS. 17 to 19, the intermediate annular rib 37 is formed over the whole periphery of the gasket 3a to uniformly project from the outer peripheral surface of the gasket 3a.

As illustrated in FIG. 18, the intermediate annular rib 37 is provided at a part defined on a side of the retaining annular rib. When the plunger 4 is strongly drawn proximally, a deformation force applied proximally to the retaining annular rib 34 is transmitted to the outer peripheral surface of the gasket 3a positioned slightly proximally from the distal end surface of the retaining annular rib 34. Therefore, the intermediate annular rib 37 is preferably positioned proximally from the distal end surface of the retaining annular rib 34. Therefore, deformation of the retaining annular rib 34 is surely prevented, abutment between the proximal end surface of the helical rib 44 and the distal end surface of the retaining annular rib 34 is surely maintained, and separation of the plunger 4 from the gasket 3a is surely prevented. In the present example, the intermediate annular rib 37 is provided at a part on the proximal side of the retaining annular rib 34, and a part defined on a side of the distal end 36c of the helical crest portion 36. Specifically, the intermediate annular rib 37 is formed on an outer surface on a side of a part defined slightly proximally from an innermost top part projecting from the retaining annular rib 34. Therefore, the intermediate annular rib is configured to have a top part positioned slightly proximally from the top part of the retaining annular rib. It is noted that the intermediate annular rib 37 comprises at least a part on a distal side from the top part, and the part is axially superposed on a part on the proximal side of the retaining annular rib 34.

Further, as illustrated in FIG. 18, the intermediate annular rib 37 is formed to be superposed on the distal end 36c of the helical crest portion 36. Additionally, as illustrated in FIG. 18, in the gasket 3a according to the present example, the distal end 36c of the helical crest portion 36 is connected to a part facing the rib absent portion 35 of the retaining annular rib 34. The intermediate annular rib 37 is disposed so that the top part thereof is positioned near the connected part (distal end 36c). In the gasket 3a according to the present example, the retaining annular rib 34 is perpendicular to the axis of the gasket 3a, and correspondingly the intermediate annular rib 37 is similarly configured.

As illustrated in FIG. 18, the intermediate annular rib 37 has an outer diameter smaller than the outer diameter of the distal side annular rib 38 and the outer diameter of the proximal side annular rib 39. Therefore, sliding resistance of the gasket 3a sliding in the barrel 2 can be reduced. Further, the outer diameter of the intermediate annular rib 37 is larger than the inner diameter of the barrel 2. Accordingly, when the plunger 4 is strongly drawn proximally, the intermediate annular rib 37 surely abuts on the inner peripheral surface of the barrel 2, and deformation of the retaining annular rib 34 can be surely inhibited. Further, the intermediate annular rib 37 has a vertical cross-section comprising a top part transversely projecting to form a chevron shape, and an end of the top part can abut on an inner surface of the barrel 2. The cross-section is formed into the chevron shape comprising the top part and a contact area between the intermediate annular rib 37 and the inner peripheral surface of the barrel 2 can be reduced. Especially, the contact area between the intermediate annular rib 37 and the inner peripheral surface of the barrel 2 is reduced relative to a contact area between the distal side annular rib 38 and the inner peripheral surface of the barrel 2 and a contact area between the proximal side annular rib 39 and the inner peripheral surface of the barrel 2, contact resistance (sliding resistance) of the gasket 3a against the barrel 2 can be reduced upon vacuum capping of the gasket 3a to the barrel 2 or upon operation of the plunger 4, and liquid tightness of the medicine 8 to be filled is secured by the distal side annular rib 38 and the proximal side annular rib 39. It is noted that for further inhibition of deformation of the retaining annular rib 34, an area of an abutment part of the intermediate annular rib making contact with the inner peripheral surface of the barrel 2 may be increased, and the intermediate annular rib may be changed to have the vertical cross-section having, for example, a rectangular shape or a semi-spherical shape so that the intermediate annular rib is sufficiently supported.

The outer diameter of the intermediate annular rib 37 is preferably larger than the inner diameter of the barrel 2 by 0 to 1.0 mm, and in particular, when the inner diameter of the barrel 2 is 8 to 10 mm, the outer diameter of the intermediate annular rib 37 is preferably larger than the inner diameter of the barrel 2 by 0.1 to 0.5 mm. Therefore, while inhibiting the deformation of the retaining annular rib 34 upon proximally drawing the plunger 4, the sliding resistance of the gasket 3a sliding in the barrel 2 can be reduced. It is noted that as long as the deformation of the retaining annular rib 34 is inhibited by abutment of the intermediate annular rib 37 on the inner peripheral surface of the barrel 2, upon proximally drawing the plunger 4 strongly, the outer diameter of the intermediate annular rib may be reduced relative to the inner diameter of the barrel 2.

In the gasket 3a according to the present example, similar to the above-mentioned gasket 3, the proximal end surface of the helical rib 44 of the plunger 4 abuts on the distal end surface of the retaining annular rib 34 of the gasket 3a, and the separation of the plunger 4 from the gasket 3a is restricted. Further, in the gasket 3a, when the plunger 4 is strongly drawn proximally, the intermediate annular rib 37 abuts on the inner peripheral surface of the barrel 2 to restrict expansion of the retaining annular rib 34 beyond a predetermined extent. Therefore, the helical rib 44 is prevented from riding over the retaining annular rib 34.

In all of the examples described above, although the height of the retaining annular rib of the gasket is different from the height of the helical rib of the plunger depending on the size or hardness of the gasket, the following are preferably employed. The height of the retaining annular rib of the gasket (inward projection length) is preferably 0.5 to 2.0 mm, in particular, 0.8 to 1.5 mm. The height of the helical rib of the plunger (outward projection length) is preferably 0.5 to 2.5 mm, in particular, 1.0 to 2.0 mm. As a component material of the plunger 4, a hard or semi-hard resin, such as a high-density polyethylene, a polypropylene, a polystyrene, a polyethylene terephthalate, is preferably used.

Further, the syringe and the prefilled syringe according to the present invention are not limited to having the gasket comprising the retaining annular rib as described above.

Figure 20:
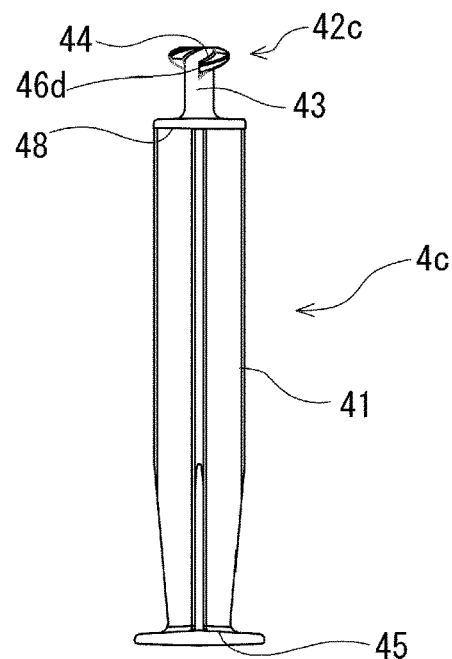
FIG. 20 is a front view of a plunger according to another example.
Figure 21:
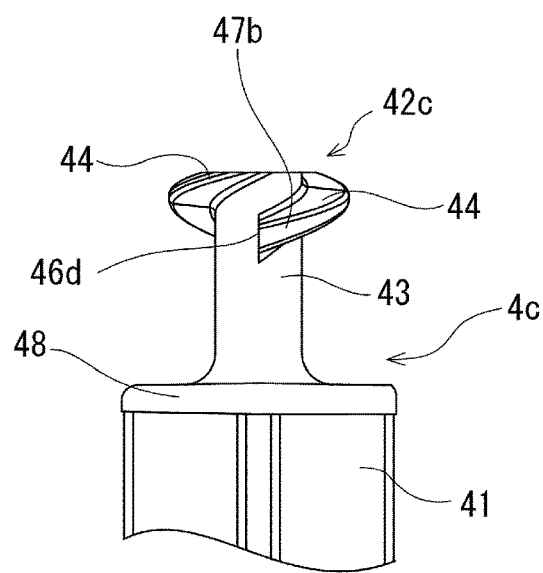
FIG. 21 is an enlarged front view of a distal end part of the plunger illustrated in FIG. 20.
Figure 22:
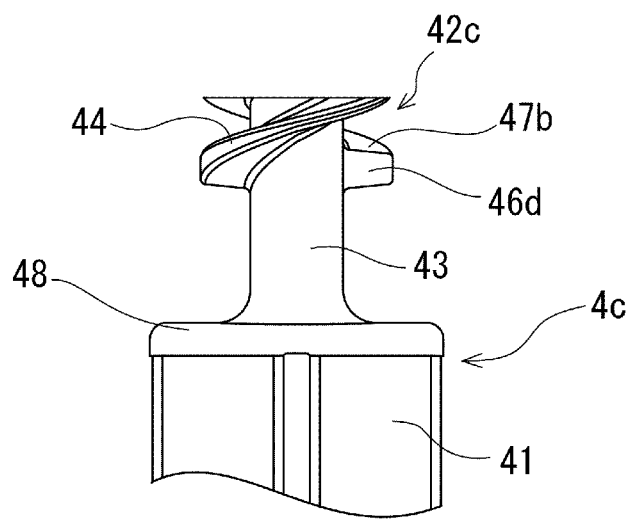
FIG. 22 is a right side view of the plunger illustrated in FIG. 21.
Figure 23:
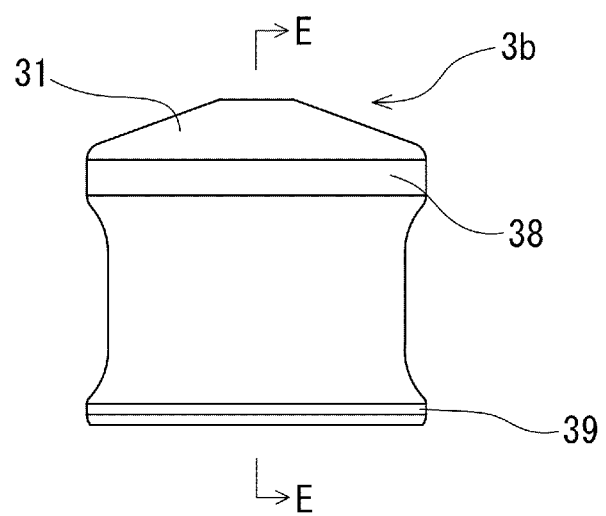
FIG. 23 is an enlarged front view of a gasket according to another example.
Figure 24:
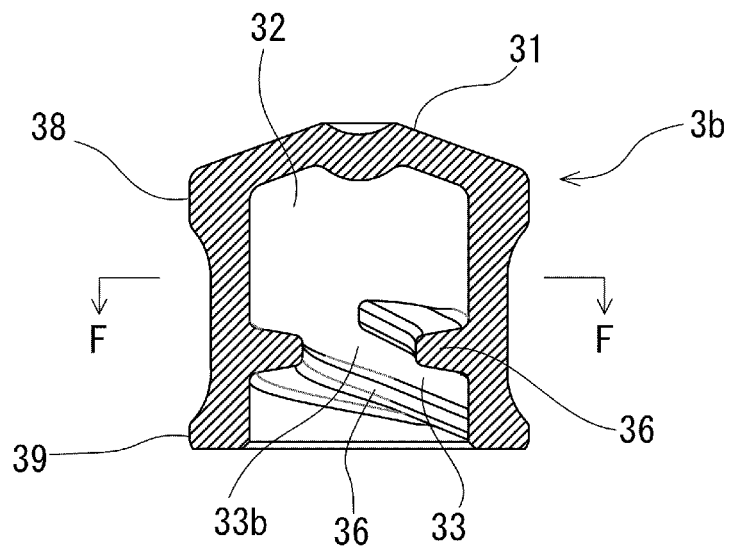
FIG. 24 is a cross-sectional view taken along the line E-E of FIG. 23.
Figure 25:
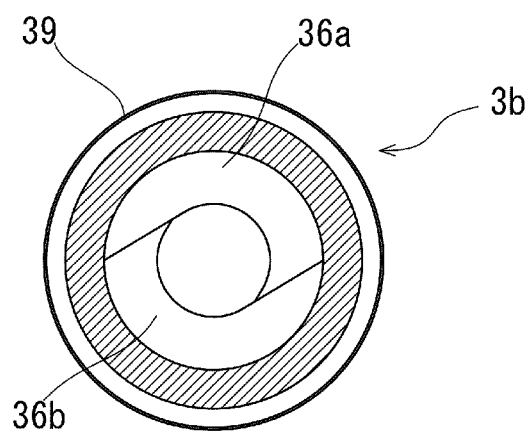
FIG. 25 is a cross-sectional view taken along the line F-F of FIG. 24.

A plunger 4c illustrated in FIGS. 20 to 22 may be employed, and a gasket 3b illustrated in FIGS. 23 to 25 may be employed.

Similar to the above-mentioned syringe, the syringe according to the present example comprises the gasket 3b comprising a cylindrical body comprising a closed distal end and an opening proximal end, and comprising the inner cavity portion 30 extending distally from the proximal side, as illustrated in FIGS. 23 to 25, the barrel 2 comprising the distal opening portion and is configured to store the gasket slidably, as illustrated in FIG. 2, and the plunger 4c comprising a head portion 42c configured to be stored in the inner cavity portion 30 of the gasket 3b slidably, as illustrated in FIGS. 20 to 22. The plunger 4c also comprises the helical ribs 44 provided at the head portion 42c, and each comprising the starting end on the distal side, and the terminal end on the proximal side.

The gasket 3b is the same as the above-mentioned gasket 3, excluding the retaining annular rib 34 and the rib absent portion 35. Therefore, the gasket 3b comprises the inner cavity portion 30, and the inner cavity portion 30 comprises the plunger-mounting function. The inner cavity portion 30 comprises, on an inner surface, the helical crest portions 36 forming the helical valley portions 33 for threadedly engaging with the helical ribs 44 of the plunger 4c, and the accommodation portion 32 positioned distally from the helical crest portions 36 and being configured to accommodate the part of the head portion 42c of the plunger 4c at which the helical ribs are formed. The helical valley portion 33 comprises the starting end near the opening portion of the inner cavity portion 30, distally extends by a predetermined length, and comprises the terminal end positioned proximally from the accommodation portion 32.

Each helical rib 44 of the plunger 4c comprises an entrance-restricting terminal end portion 47b for restricting the entrance of the helical rib 44 into the distal end 33b of the helical valley portion 33, after storage of the part of the plunger 4c at which the helical ribs are formed, in the accommodation portion 32 of the gasket 3b. The entrance-restricting terminal end portion 47b is formed as a thick terminal end portion 47b having a width larger than that of the distal end 33b of the helical valley portion 33. The thick terminal end portion 47b is configured to expand the helical crest portion 36 to pass through the helical valley portion 33, and after the passage, entrance of the thick terminal end portion 47b into the distal end 33b of the helical valley portion 33 is made substantially impossible.

In the present example, as illustrated in FIGS. 20 to 22 and FIG. 26, the helical rib 44 has a thickness formed to be increased gradually toward the terminal end. Therefore, the terminal end has the largest thickness. The helical rib 44 may have a thickness largest only at the terminal end part, or a thickness substantially uniform at the distal end part and gradually increased from the center part to the terminal end part. Further, in the present example, the thick terminal end portion 47b of the helical rib 44 comprises a terminal end surface 46d formed as the rising terminal end surface 46d extending parallel to the axis of the shaft portion 43. Therefore, the terminal end surface 46d is configured to have an area equal to the thickness of the thick terminal end portion 47b. The helical rib 44 in the present example has a thickness reduced gradually toward an outer end thereof on the distal side. However, as illustrated in FIG. 22, the thick terminal end portion 47b has a trapezoidal cross-section to have a sufficient thickness even at the outer end. Therefore, the terminal end surface 46d also has the trapezoidal cross-section to have a sufficient width even at the outer end. The thickness of the thick terminal end portion 47b, i.e., a height of the terminal end surface 46d (axial length to the axis of the shaft portion 43) is configured to be larger than a height of the distal end 33b of the helical valley portion 33 (axial length to the axis of the gasket 3b). Therefore, entrance of the terminal end of the thick terminal end portion 47b into the distal end 33b of the helical valley portion 33 is inhibited.

The rising terminal end surface 46d is preferably parallel to the axis of the shaft portion 43, but may be slightly oblique to the axis. In this configuration, the rising terminal end surface 46d is preferably inclined to the proximal side (disk portion 48 side). Further the rising terminal end surface 46d preferably comprises a flat surface, but may have an uneven surface or a curved surface.

Figure 26:
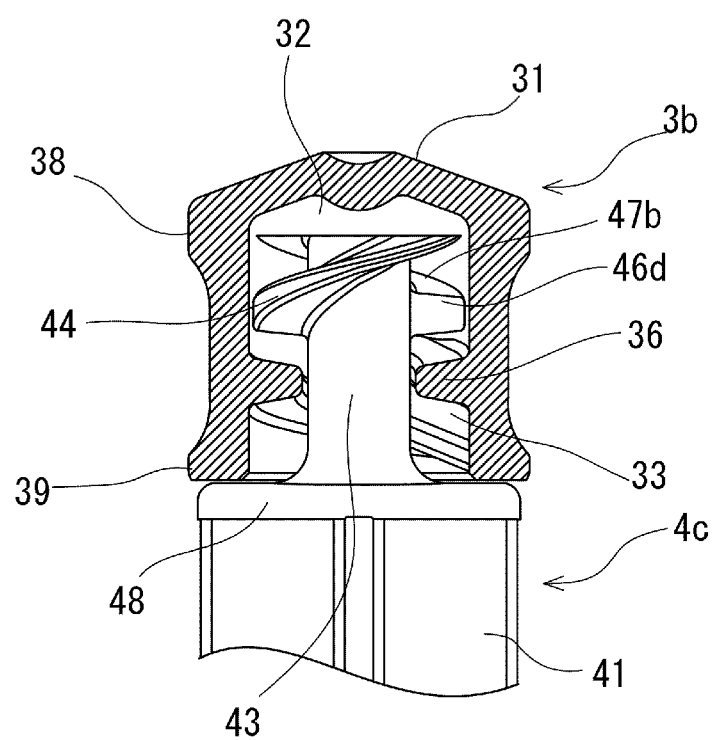
FIG. 26 is a schematic diagram illustrating an effect upon mounting a gasket and a plunger in a syringe using the plunger illustrated in FIGS. 20 to 22 and the gasket illustrated in FIGS. 23 to 25.

Similar to the above-mentioned examples, even in the plunger 4c and the gasket 3b, after the helical rib 44 of the plunger 4c is inserted into the proximal end of the helical valley portion 33 of the gasket 3b, the plunger 4c is turned to advance the threaded engagement between the helical rib 44 and the helical valley portion 33. The thick terminal end portion 47b is advanced through the helical valley portion 33, while slightly expanding the helical crest portion 36. When the plunger 4c keeps turning, the helical rib 44 passes through the helical valley portion 33 and enters the accommodation portion 32, and as illustrated in FIG. 26, the whole of the helical rib 44, i.e., the part of the head portion 42c of the plunger 4c at which the helical ribs are formed, is configured to be stored in the accommodation portion 32 of the gasket 3b.

While the plunger 4c is mounted to the gasket 3b, in the helical rib 44 of the plunger 4c, the proximal end surface 46d of the thick terminal end portion 47b abuts on the distal end surface of the helical crest portion 36. Therefore, separation of the plunger 4c from the gasket 3b is restricted. When operation that is not performed usually, such as turning the plunger 4c as it is drawn proximally, is performed, the thick terminal end portion 47b of the helical rib 44 does not enter the proximal end 33b of the helical valley portion 33. Therefore, even if the special operation as described above is performed, separation of the plunger from the gasket is prevented.

Figure 9:
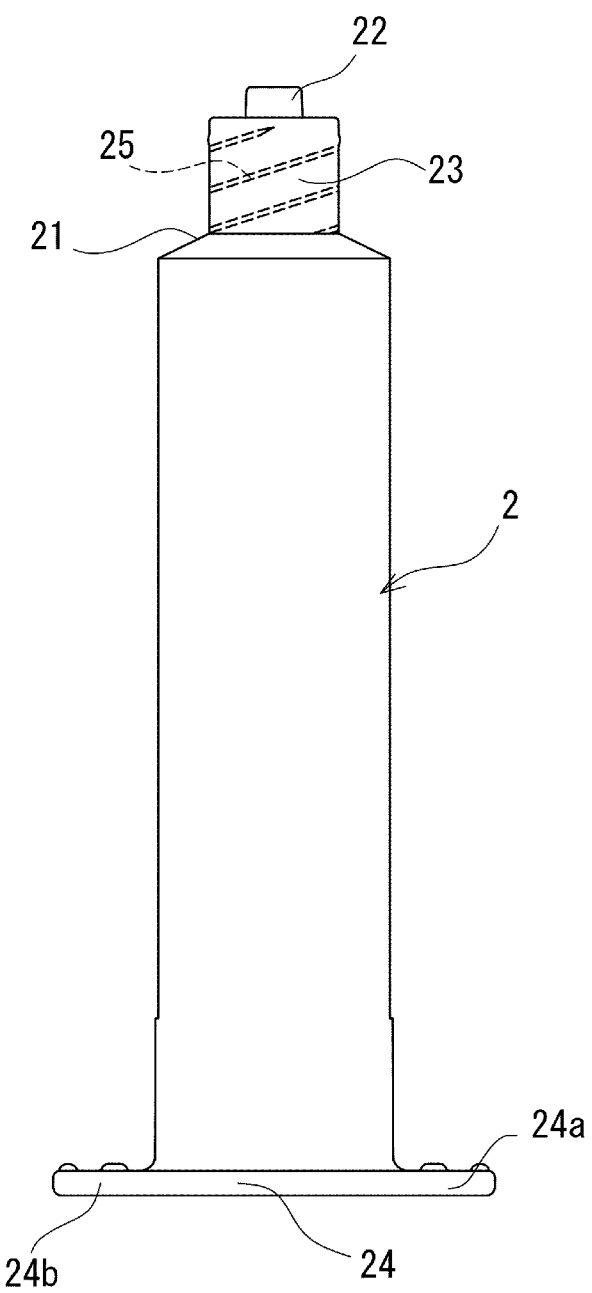
FIG. 9 is a front view of one example of a barrel used for a syringe according to the first embodiment of the present invention.

The barrel 2 comprises a cylindrical body comprising a transparent or translucent material, preferably a material having reduced oxygen permeability or water vapor permeability. As illustrated in FIGS. 2 and 9, the barrel 2 comprises a nozzle portion 22 and a collar 23. The nozzle portion 22 is provided at a distal end of the barrel 2, comprises the distal opening portion for ejecting the liquid medicine or the like in the barrel, and is formed to have a diameter distally reduced into a tapered shape. The collar 23 is formed concentrically with the nozzle portion 22 into a cylindrical shape to surround the nozzle portion 22. Further, the collar 23 comprises an opening distal end, and the collar 23 has substantially constant inner and outer diameters each from the proximal end (barrel distal end surface 21) to the distal end. Further, a distal end part of the nozzle portion 22 projects from the opening distal end of the collar 23, and the nozzle portion 22 and the collar 23 have distal end parts chamfered to facilitate the storage of the nozzle portion 22 and the collar 23 in the sealing member (sealing cap) 5.

The collar 23 comprises an inner peripheral surface in which a thread groove (helical valley portion on the barrel side) 25 is formed for threaded engagement with a thread (helical crest portion on the cap side) 54 formed on a below-mentioned nozzle accommodation portion 53 of the sealing cap 5. Therefore, the barrel 2 and the sealing cap 5 are threadedly engaged between the inner peripheral surface of the collar 23 and an outer peripheral surface of the nozzle accommodation portion 53. Further, the thread groove (helical valley portion on the barrel side) 25 serves as a portion for mounting an injection needle (hub for the injection needle), after the sealing cap 5 is removed from the barrel. As illustrated in FIGS. 1 and 2, and 9, the barrel comprises a flange 24. The flange 24 is the disk portion having an elliptical torus shape formed to project perpendicularly from the whole circumference of the proximal end of the barrel 2. As illustrated in FIGS. 1, 2, and 9, the flange 24 comprises two opposed grip portions 24a and 24b having a wide width, and the grip portion comprises a distal side on which a plurality of ribs is formed.

Figure 10:
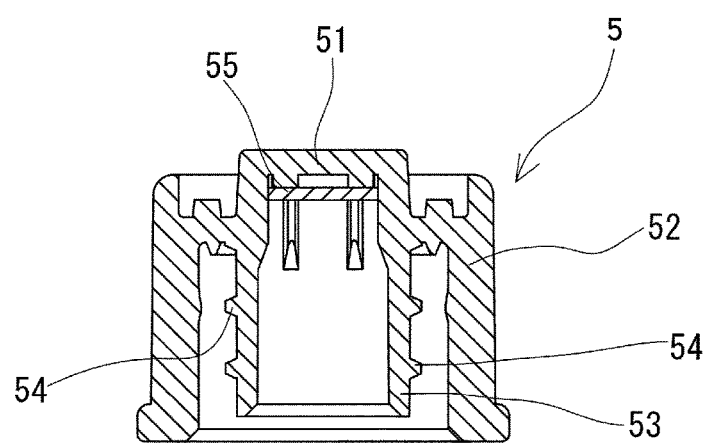
FIG. 10 is a cross-sectional view of one example of a sealing cap used for a syringe according to the first embodiment of the present invention.

A material of the barrel 2 includes, for example, a resin, such as a polypropylene, a polyethylene, a polystyrene, a polyamide, a polycarbonate, a polyvinyl chloride, poly(4-methyl pentene-1), an acrylic resin, an acrylonitrile-butadiene-styrene copolymer, a polyester, such as a polyethylene terephthalate, or a cyclic polyolefin. In particular, the resin, such as a polypropylene or a cyclic polyolefin, is preferably employed for easy moldability and heat resistance. As illustrated in FIGS. 1, 2, and 10, the sealing cap 5 as the sealing member comprises a closed end 51, the nozzle accommodation portion 53, and a collar accommodation portion 52.

The nozzle accommodation portion 53 is provided at a center part of the sealing cap 5, has a closed distal end, and formed into a cylindrical shape. The nozzle accommodation portion 53 has an inner diameter formed slightly larger than that of the nozzle portion 22, the inner diameter is configured to be slightly increased toward the proximal end from the distal end into a tapered shape, and store the whole nozzle portion 22 from a proximal opening. The nozzle accommodation portion 53 comprises an inside closed surface (inner surface of the closed end 51) on which a sealing member 55 for liquid-tightly sealing the distal opening portion of the barrel 2 is stored. The sealing member 55 preferably includes an elastic member for liquid-tightly sealing the distal opening portion of the barrel 2. A material of the sealing member preferably includes, for example, natural rubber, a synthetic rubber, such as an isoprene rubber, a butadiene rubber, a fluoro-rubber, a silicone rubber, or a thermoplastic elastomer such as an olefinic elastomer or a styrene elastomer. Further, the nozzle accommodation portion 53 comprises an outer surface on which the thread (helical crest portion on the cap side) 54 is formed for threaded engagement with the thread groove (helical valley portion on the barrel side) 25 formed on an inner surface of the collar 23 of the barrel 2 is formed. Therefore, the barrel 2 and the sealing cap 5 are threadedly engaged with each other between the outer surface of the nozzle accommodation portion 53 and the inner surface of the collar 23.

The collar accommodation portion 52 comprises a cylindrical body formed to surround the nozzle accommodation portion 53 and comprising a closed distal end, and stores the collar 23 between an inner surface of the collar accommodation portion 52 and the outer surface of the nozzle accommodation portion 53. Further, the collar accommodation portion 52 formed into a cylindrical shape is concentric with the nozzle accommodation portion 53, and the collar accommodation portion 52 has an inner diameter having a substantially constant diameter from the distal end to the proximal end. Further, as illustrated in FIG. 1, the sealing cap 5 comprises an outside surface (outer peripheral surface of the collar accommodation portion 52) which is vertically knurled to prevent slip of fingers or the like upon turning the sealing cap 5. A material of the sealing cap 5 includes for example a resin, such as a polypropylene, a polyethylene, a polystyrene, a polyamide, a polycarbonate, a polyvinyl chloride, poly(4-methyl pentene-1), an acrylic resin, an acrylonitrile-butadiene-styrene copolymer, a polyester, such as polyethylene terephthalate, or a cyclic polyolefin. In particular, the resin, such as a polypropylene or a cyclic polyolefin, is preferably employed for easy moldability and heat resistance.

As illustrated in FIGS. 1 and 2, the prefilled syringe 1 according to the present invention comprises the above-mentioned syringe 10, the sealing member 5 for sealing the distal opening portion of the barrel 2, and the medicine 8 filled in a space formed by the gasket 3. The medicine 8 may include any medicine, for example, a liquid medicine, such as a cyclosporine, a benzodiazepine, a sodium chloride injection solution, a vitamin preparation, or a mineral, a solvent, such as a physiological saline solution, or a powdered or freeze-dried medicine or a liquid medicine, such as an antibiotic or a protein preparation. The prefilled syringe according to the present invention is particularly suitable for a prefilled syringe filled with a solvent for dissolving a medicine stored in a vial. Such a solvent includes a physiological saline solution, injection water, a glucose solution, or the like.

The syringe according to certain embodiments of the present invention comprises the following.

(1) A syringe comprising a gasket being a cylindrical body comprising a closed distal end and an opening proximal end, the gasket comprising an inner cavity portion extending distally from a proximal side. The syringe further comprises a barrel comprising a distal opening portion, the barrel configured to store the gasket slidably, and a plunger comprising a head portion configured to be stored in the inner cavity portion of the gasket. The plunger comprises a helical rib provided at the head portion and comprising a starting end on a distal side and a terminal end on a proximal side. The gasket comprises, on an inner surface of the inner cavity portion, a helical crest portion forming a helical valley portion threadedly engaged with the helical rib of the plunger, and a plunger-retaining annular rib positioned distally from the helical crest portion. The inner cavity portion further comprises an accommodation portion positioned distally from the retaining annular rib, the accommodation portion configured to store the part of the head portion of the plunger at which the helical rib is formed. The retaining annular rib further comprises a rib absent portion for guiding, to the accommodation portion, the helical rib reaching the retaining annular rib as threaded engagement is advanced between the plunger and the gasket. The plunger comprises, at the terminal end of the helical rib, an entrance-restricting terminal end portion for restricting the entrance of the helical rib into the rib absent portion, after storage of a part of the plunger at which the helical rib is formed, in the accommodation portion of the gasket.

Certain embodiments of the syringe may comprise the following.

(2) The syringe according to (1), in which the helical crest portion comprises a distal end connected to a part of the retaining annular rib adjacent to the rib absent portion, and a surface on the distal side of the distal end part of the helical crest portion is adjacent to a proximal end of the rib absent portion.

(3) The syringe according to (1) or (2), in which the gasket comprises, on an outer peripheral surface, a distal side annular rib having an outer diameter larger than an inner diameter of the barrel, a proximal side annular rib having an outer diameter larger than the inner diameter of the barrel, and an intermediate annular rib provided between the distal side annular rib and the proximal side annular rib, and further the intermediate annular rib is provided at a part defined on a side of the retaining annular rib.

(4) The syringe according to (3), in which the intermediate annular rib comprises an outer diameter configured to be smaller than the outer diameter of the distal side annular rib and the outer diameter of the proximal side annular rib.

(5) The syringe according to (4), in which the intermediate annular rib comprises the outer diameter larger than the inner diameter of the barrel.

(6) The syringe according to (5), in which a contact area between the intermediate annular rib and an inner peripheral surface of the barrel is smaller than a contact area between the distal side annular rib and the inner peripheral surface of the barrel, and a contact area between the proximal side annular rib and the inner peripheral surface of the barrel.

(7) The syringe according to any of (3) to (6), in which the intermediate annular rib comprises a vertical cross-section comprising a top part, and formed into a chevron shape.

(8) The syringe according to any of (3) to (7), in which the intermediate annular rib is provided to have an outermost projecting top part positioned at a side part on a proximal side of the retaining annular rib.

Further, the syringe according to certain embodiments of the present invention comprises the following.

(9) A syringe comprising a gasket being a cylindrical body comprising a closed distal end and an opening proximal end, the gasket comprising an inner cavity portion extending distally from a proximal side. The syringe further comprises a barrel comprising a distal opening portion and configured to store the gasket slidably, and a plunger comprising a head portion configured to be stored in the inner cavity portion of the gasket. The plunger comprises a helical rib provided at the head portion and comprising a starting end on a distal side and a terminal end on a proximal side. The gasket comprises, on an inner surface of the inner cavity portion, a helical crest portion forming a helical valley portion threadedly engaged with the helical rib of the plunger, and an accommodation portion positioned distally from the helical crest portion, the accommodation portion configured to store the part of the head portion of the plunger at which the helical rib is formed. The helical valley portion comprises a starting end near an opening portion of the inner cavity portion, distally extending by a predetermined length, and comprises a terminal end positioned proximally from the accommodation portion. The plunger comprises, at the terminal end of the helical rib, an entrance-restricting terminal end portion for restricting the entrance of the helical rib into the terminal end of the helical valley portion, after storage of a part of the plunger at which the helical rib is formed, in the accommodation portion of the gasket.

Certain embodiments of the syringe may comprise the following.

(10) The syringe according to any of (1) to (9), in which the head portion comprises a shaft portion comprising the helical rib on an outer surface, and the entrance-restricting terminal end portion of the helical rib comprises a rising terminal end surface formed at the terminal end of the helical rib, and extending substantially parallel to an axis of the shaft portion.

(11) The syringe according to any of (1) to (9), in which the head portion comprises a shaft portion comprising the helical rib on an outer surface, and the entrance-restricting terminal end portion of the helical rib comprises an inclined terminal end surface for entrance restriction, formed at the terminal end of the helical rib, and positioned obliquely by a predetermined angle relative to an axis of the shaft portion to extend a surface on the distal side of the helical rib longer in the circumferential direction of the shaft portion than a surface on the proximal side of the helical rib.

(12) The syringe according to any of (1) to (11), in which the head portion comprises the shaft portion comprising the helical rib on the outer surface, the entrance-restricting terminal end portion of the helical rib comprises a circumferentially extending portion provided at a proximal end of the helical rib and extending to the terminal end of the helical rib in a circumferential direction of the shaft portion to have a helical inclination smaller than that of a part on the distal side of the helical rib, or to be substantially perpendicular to the axis of the shaft portion.

(13) The syringe according to any of (9) to (12), in which the entrance-restricting terminal end portion comprises a thick terminal end portion having a width larger than that of the terminal end of the helical valley portion, in an axial direction of the gasket, the thick terminal end portion configured to expand the helical valley portion for passage, and after the passage, entrance of the thick terminal end portion into the terminal end of the helical valley portion is made substantially impossible.

(14) The syringe according to any of (1) to (13), in which the syringe is a prefilled syringe.

Further, the prefilled syringe according to certain embodiments of the present invention comprises the following.

(15) A prefilled syringe comprising a syringe according to any of (1) to (14), a sealing member for sealing a distal opening portion of a barrel, and a medicine stored in the barrel.

What is claimed is:
1. A syringe comprising:
a cylindrically-shaped gasket comprising a closed distal end, an open proximal end, and an inner cavity portion extending distally from a proximal side;
a barrel comprising a distal opening portion and configured to slidably contain the gasket; and
a plunger comprising a head portion configured to be contained in the inner cavity portion of the gasket,
wherein the head portion comprises:
a shaft portion, and
a helical rib located at an outer surface of the shaft portion, the helical rib comprising a starting end on a distal side and a terminal end on a proximal side,
wherein the gasket comprises, on an inner surface of the inner cavity portion, a helical crest portion forming a helical valley portion configured to threadedly engage with the helical rib of the plunger, and a plunger-retaining annular rib positioned distally from the helical crest portion, wherein the inner cavity portion further comprises an accommodation portion positioned distally from the plunger-retaining annular rib, the accommodation portion configured to contain a part of the head portion of the plunger at which the helical rib is formed, and wherein the plunger-retaining annular rib further comprises a rib absent portion configured to guide, to the accommodation portion, the helical rib reaching the plunger-retaining annular rib as threaded engagement is advanced between the plunger and the gasket,
wherein the plunger comprises, at the terminal end of the helical rib, an entrance-restricting terminal end portion configured to restrict the entrance of the helical rib into the rib absent portion after the part of the plunger at which the helical rib is formed is contained in the accommodation portion of the gasket,
wherein the helical rib includes a proximal surface extending outward from the shaft portion, a distal surface extending outward from the shaft portion, and an outer surface extending between the proximal surface to the distal surface, and wherein the entrance-restricting terminal end portion comprises a terminal end surface that extends (i) between the proximal surface of the helical rib and the distal surface of the helical rib, and (ii) between the shaft portion and the outer surface of the helical rib.

2. The syringe according to claim 1, wherein the helical crest portion comprises a distal end connected to a part of the plunger-retaining annular rib adjacent to the rib absent portion, and wherein a surface on a distal end part of the helical crest portion is adjacent to a proximal end of the rib absent portion.

3. The syringe according to claim 1, wherein the gasket comprises, on an outer peripheral surface, a distal side annular rib having an outer diameter larger than an inner diameter of the barrel, a proximal side annular rib having an outer diameter larger than the inner diameter of the barrel, and an intermediate annular rib provided between the distal side annular rib and the proximal side annular rib and further provided at a part defined on a side of the plunger-retaining annular rib.

4. The syringe according to claim 3, wherein the intermediate annular rib has an outer diameter smaller than the outer diameter of the distal side annular rib and the outer diameter of the proximal side annular rib.

5. The syringe according to claim 1, wherein the terminal end surface extends substantially parallel to an axis of the shaft portion.

6. The syringe according to claim 1, wherein the terminal end surface extends obliquely to an axis of the shaft portion by a predetermined angle such that, at the entrance-restricting terminal end portion, a distance by which the distal surface of the helical rib extends around the shaft portion is greater than a distance by which the proximal surface of the helical rib extends around the shaft portion.

7. The syringe according to claim 1, wherein the proximal side of the helical rib comprises a circumferentially extending portion that extends to the terminal end of the helical rib in a circumferential direction around the shaft portion, the circumferentially extending portion having a helical inclination smaller than that of a part on the distal side of the helical rib or being substantially perpendicular to an axis of the shaft portion.

8. The syringe according to claim 1, wherein the syringe is a prefilled syringe.

9. A prefilled syringe comprising:
a syringe according to claim 1;
a sealing member for sealing the distal opening portion of the barrel; and
a medicine contained in the barrel.

10. A syringe comprising:
a cylindrically-shaped gasket comprising a closed distal end and an opened proximal end, and an inner cavity portion extending distally from a proximal side;
a barrel comprising a distal opening portion and configured to slidably contain the gasket; and
a plunger comprising a head portion configured to be contained in the inner cavity portion of the gasket, wherein the plunger comprises a helical rib provided at the head portion, the helical rib comprising a starting end on a distal side and a terminal end on a proximal side, wherein the gasket comprises, on an inner surface of the inner cavity portion, a helical crest portion forming a helical valley portion configured to threadedly engage with the helical rib of the plunger, and an accommodation portion positioned distally from the helical crest portion, the accommodation portion configured to contain a part of the head portion of the plunger at which the helical rib is formed, wherein the helical valley portion comprises a starting end disposed near an opening portion of the inner cavity portion and distally extending by a predetermined length, and a terminal end positioned proximally from the accommodation portion, and wherein the plunger comprises, at the terminal end of the helical rib, an entrance-restricting terminal end portion configured to restrict the entrance of the helical rib into the terminal end of the helical valley portion after the part of the plunger at which the helical rib is formed is contained in the accommodation portion of the gasket, wherein the entrance-restricting terminal end portion comprises a thick terminal end portion of the helical rib, a width of the thick terminal end portion in an axial direction of the plunger being larger than a width of the helical valley portion in an axial direction of the gasket, and wherein the thick terminal end portion is configured to expand the helical valley portion during passage through the helical valley portion, and after the passage, entrance of the thick terminal end portion into the terminal end of the helical valley portion is inhibited by the thick terminal end portion.

11. The syringe according to claim 10, wherein the helical rib includes a proximal surface extending outward from the shaft portion, a distal surface extending outward from the shaft portion, and an outer surface extending between the proximal surface to the distal surface, and wherein the entrance-restricting terminal end portion comprises a terminal end surface that extends (i) between the proximal surface of the helical rib and the distal surface of the helical rib, and (ii) between the shaft portion and the outer surface of the helical rib.

* * * * *